United States Patent
Luo et al.

(10) Patent No.: US 11,090,074 B2
(45) Date of Patent: Aug. 17, 2021

(54) DOUBLE-PURPOSE FORCEPS

(71) Applicants: SHANGHAI REACH MEDICAL INSTRUMENT CO., LTD., Shanghai (CN); THE FOURTH MILITARY MEDICAL UNIVERSITY OF THE CHINESE PEOPLE'S LIBERATION ARMY, Xi'an (CN)

(72) Inventors: Zhuojing Luo, Xi'an (CN); Xiaomin Huang, Shanghai (CN)

(73) Assignees: The Fourth Military Medical University of The Chinese People's Liberation Army, Xian (CN); Shanghai Reach Medical Instrument Co., Ltd., Shanghai (CN)

( * ) Notice: Subject to any disclaimer, the term of this patent is extended or adjusted under 35 U.S.C. 154(b) by 3 days.

(21) Appl. No.: 16/628,010

(22) PCT Filed: Aug. 14, 2018

(86) PCT No.: PCT/CN2018/100315
§ 371 (c)(1),
(2) Date: Dec. 31, 2019

(87) PCT Pub. No.: WO2019/134365
PCT Pub. Date: Jul. 11, 2019

(65) Prior Publication Data
US 2020/0214730 A1    Jul. 9, 2020

(30) Foreign Application Priority Data

Jan. 5, 2018 (CN) .......................... 201810013118.6

(51) Int. Cl.
*A61B 17/28* (2006.01)
*A61B 17/92* (2006.01)
*A61B 17/56* (2006.01)

(52) U.S. Cl.
CPC .......... *A61B 17/2812* (2013.01); *A61B 17/92* (2013.01); *A61B 2017/564* (2013.01); *A61B 2017/922* (2013.01)

(58) Field of Classification Search
CPC ...... A61B 2017/00353; A61B 17/2804; A61B 17/2812; A61B 17/2816;
(Continued)

(56) References Cited

U.S. PATENT DOCUMENTS

| 5,865,075 | A | * | 2/1999 | Medved ................ B25B 27/205 81/302 |
| 5,873,858 | A | * | 2/1999 | Schafer ............. A61M 25/0668 604/161 |

(Continued)

FOREIGN PATENT DOCUMENTS

| CN | 202154741 | 3/2012 |
| CN | 204072230 | 1/2015 |

(Continued)

OTHER PUBLICATIONS

International Search Report in PCT/CN2018/100315, issued by ISA, dated Nov. 7, 2019.

(Continued)

*Primary Examiner* — Zade Coley
(74) *Attorney, Agent, or Firm* — Zhu Lehnhoff LLP

(57) ABSTRACT

The invention provides a pair of dual-purpose forceps, comprising a first forceps body and a second forceps body. When the first forceps body is connected with the second forceps body by means of a first pressurizing connecting member and a second pressurizing connecting member, a first handheld member and a second handheld member move towards each other, and a first pressurizing functional member and a second pressurizing functional member also move towards each other to complete pressurizing; when the first (Continued)

forceps body is connected with the second forceps body by means of a first opening connecting member and a second opening connecting member, the first handheld member and the second handheld member move towards each other, and a first opening function member and a second opening function portion face away from each other to complete opening. The dual-purpose forceps is simple in structure and is operated conveniently so that the double-purpose forceps can switch freely between opening and pressurizing functions conveniently and quickly.

20 Claims, 4 Drawing Sheets

(58) Field of Classification Search
CPC .......... A61B 2017/2947; A61B 17/28–17/295; B25B 7/06; B25B 7/10; B25B 7/18
See application file for complete search history.

(56) References Cited

U.S. PATENT DOCUMENTS

| | | |
|---|---|---|
| 10,441,337 B2 | 10/2019 | Paulisch et al. |
| 2008/0027461 A1* | 1/2008 | Vaquero ................ A61F 2/1664 |
| | | 606/107 |
| 2009/0259262 A1 | 10/2009 | Nayet |
| 2018/0103995 A1* | 4/2018 | Ding .................. A61B 18/1442 |

FOREIGN PATENT DOCUMENTS

| | | | |
|---|---|---|---|
| CN | 204581366 | 8/2015 | |
| CN | 205411275 | 8/2016 | |
| CN | 106214194 | 12/2016 | |
| CN | 108210060 | 6/2018 | |
| WO | WO-8903283 A1 * | 4/1989 | .............. B25B 7/00 |
| WO | WO-8903283 A1 * | 2/2021 | |

OTHER PUBLICATIONS

Written Opinion of the International Search Report in PCT/CN2018/100315, issued by ISA, dated Nov. 7, 2019.

* cited by examiner

DOUBLE-PURPOSE FORCEPS

TECHNICAL FIELD

The invention relates to the technical field of orthopedic medical devices and tools, in particular to dual-purpose forceps.

BACKGROUND

With the development of spinal internal fixation operation, a spinal screw rod fixation system is used to reposition and correct the injured spine, and applied more and more widely; lots of pedicle screws are required to fix spines in the operation process, and the screw positions need regulating by means of medical forceps. Existing medical forceps have only opening function or pressurizing function, while medical forceps capable of switching different functions continuously are required to regulate the screw positions in the actual operation process. In this way, not only is the operation complex, but also the number of the medical forceps is increased in operation so that the medical cost is increased.

SUMMARY OF THE INVENTION

The invention aims to provide a pair of dual-purpose forceps with the advantages of the simple structure and capability of freely switching between the opening and pressurizing functions conveniently and efficiently.

In order to solve the above technical problems, the invention relates to a pair of dual-purpose forceps, comprising a first forceps body comprising a first handheld member, a first pressurizing functional member and a first opening function member; a first pressurizing connecting member and an opening connection portion are arranged at the transition area between the first handheld member and the first pressurizing functional member as well as between the first handheld member and the first opening function member; a second forceps body comprising a second handheld member, and a second pressurizing functional member and a second opening function portion which correspond to the first pressurizing functional member and the first opening function member; a second pressurizing connecting member and an opening connection portion are arranged at the transition areas between the second handheld member and the second pressurizing functional member as well as between the second handheld member and the second opening function portion. The second pressurizing connecting member and the second opening connecting member correspond to the first pressurizing connecting member and the first opening connecting member. When the first forceps body is connected with the second forceps body through the first pressurizing connecting member and the second pressurizing connecting member, the first handheld member and the second handheld member move towards each other, and the first pressurizing functional member and the second pressurizing functional member also move towards each other to complete pressurizing; when the first forceps body is connected with the second forceps body through the first opening connecting member and the second opening connecting member, the first handheld member and the second handheld member move towards each other, and the first opening function member and the second opening function portion face away from each other to complete opening.

The dual-purpose forceps provided by the invention are simple in structure, and can be conveniently and efficiently switched between the opening and pressurizing functions through engagement and disengagement of the pressurizing connection portion and the opening connection portion.

As the further improvement of the invention, the shape of the first pressurizing functional member located on the first forceps body is arranged to an arc, and the shape of the first opening function member is arranged to an approximate straight line; the shape of the second pressurizing functional member and the second opening function portion are symmetrical to the shape of the first pressurizing functional member and the first opening function member.

When the forceps are switched between the opening and pressurizing functions, the proper end shape can control the rod more effectively and quickly.

As the further improvement of the invention, the first pressurizing connecting member and the second pressurizing connecting member as well as the first opening connecting member and the second opening connecting member are connected through an articulated shaft.

The connection portions of the forceps bodies are connected through the articulated shaft, and the structure is simple; the removal and installation process is convenient and efficient.

As the further improvement of the invention, the outer edge of the head of the articulated shaft is arranged to be non-circular, and the outer edge of at least one of two corresponding hinge holes connected through one articulated shaft is arranged to be non-circular coinciding with the outer edge of the head of the articulated shaft.

The outer edge of the head of the articulated shaft and at least one hinge hole corresponding to the articulated shaft adopt non-circular design, and coincide with each other. Such design enables the articulated shaft to conveniently and efficiently disengage or engage with the corresponding hinge hole in the function switching process of the forceps, and the articulated shaft is not liable to escape from the hinge holes in the using process and after disengagement and engagement.

As the further improvement of the invention, the non-circular is rhombus preferably.

As the further improvement of the invention, wear resistant layers are arranged on the inner walls of the hinge holes.

The wear resistant layers arranged on the inner walls of the hinge holes reduce wear of the inner walls of the hinge holes effectively, and ensure the service life and accuracy of the forceps.

As the further improvement of the invention, the clamping slots which are perpendicular to the working faces of the first pressurizing functional member and the first opening function member are arranged in the first pressurizing functional member and the first opening function member, and corresponding clamping slots are also arranged in the second pressurizing functional member and the second opening function portion.

As the further improvement of the invention, the clamping slots are arranged to a U shape.

The clamping slots corresponding up and down are arranged in the ends of the function portions of the two forceps bodies so that control over the rod by the forceps is more convenient and accurate.

As the further improvement of the invention, relief slots or relief holes are arranged in the first handheld member and the second handheld member.

The relief slots or the relief holes arranged in the handheld portions of the forceps bodies reduce the dead weight of the forceps on the premise of meeting the requirement of service strength of the forceps so that the physical load and fatigue of operation personnel are reduced.

As the further improvement of the invention, the first forceps body and the second forceps body are made from the ixef 1022 plastic.

BRIEF DESCRIPTION OF THE DRAWINGS

In order to describe the embodiments of the invention or the technical scheme in the prior art more clearly, a brief introduction to the drawings required to use in the embodiment or the description of the prior art is made below, and obviously the drawings in the following description are only some embodiments of the invention; for those skilled in the art, on the premise that no creative work is done, other drawings can be further obtained according to these drawings.

DETAILED DESCRIPTION OF THE PREFERRED EMBODIMENTS

Figure 1:
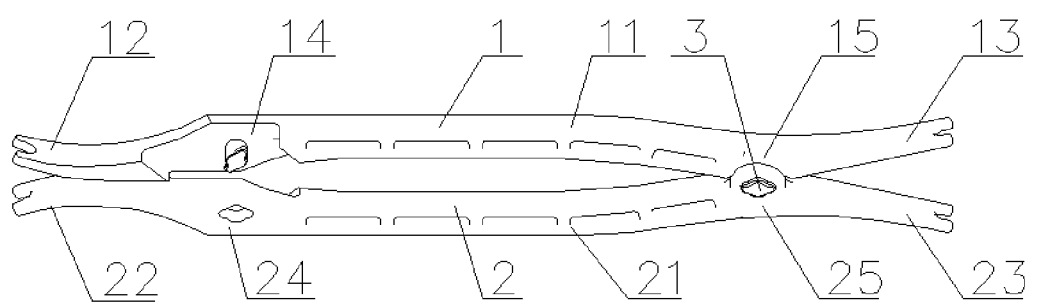
FIG. 1 is a structure diagram of the dual-purpose forceps.

A detailed description of the dual-purpose forceps of the invention is given below in combination with the embodiments of the invention:

In order to achieve the purposes of the invention, FIG. 1 shows a three-dimensional structure diagram of the dual-purpose forceps. The dual-purpose forceps comprise two forceps bodies which are connected with each other through the articulated shaft and can be moved freely, and the two forceps bodies include a first forceps body and a second forceps body. Except for the connection mode of the articulated shaft, other proper connection modes can be also adopted certainly. The first forceps body 1 and the second forceps body 2 are made from the ixef 1022 plastic. The relief slots or the relief holes can be arranged in the forceps bodies 1 and 2, and in this way the dead weight of the forceps is reduced greatly on the premise of meeting the requirement of service strength of the forceps so that the physical load and fatigue of operation personnel are reduced. The hinge holes are arranged in the first pressurizing connecting member 14 and the first opening connecting member 15 of the first forceps body 1, and correspondingly the hinge holes are arranged in the second pressurizing connecting member 24 and the second opening connecting member 25 of the first forceps body 2; the positions of the hinge holes in the first forceps body 1 correspond to the positions of the hinge holes in the second forceps body 2 one by one separately; and the articulated shaft is used to disengage or engage the two forceps bodies 1 and 2. The outer edge of the head of the articulated shaft 3 is arranged to be non-circular, and the outer edge of at least one of two corresponding hinge holes connected through the articulated shaft is arranged to be non-circular coinciding with the outer edge of the head of the articulated shaft, and the non-circular is rhombus preferably, and can also be any other proper shape. The outer edge of the head of the articulated shaft the corresponding hinge holes coincide with each other, and have a certain rational clearance. Such design enables the articulated shaft 3 to conveniently and efficiently insert into or separate from the corresponding hinge hole in the function switching process of the forceps, and the forceps is facilitated to freely switch between the opening and pressurizing functions; the articulated shaft 3 is not liable to escape from the hinge holes in the using process and after disengagement and engagement. In order to avoid the situation that the hinge holes are worn in the long-time use process and consequently the service life of the forceps is shortened and the accuracy of the forceps is reduced, the wear resistant layers can be arranged on the inner walls of the hinge holes. In order to facilitate control over the rod, the shape of the first pressurizing functional member 12 of the first forceps body 1 is arranged to an arc, and the shape of the first opening function member 13 is arranged to a line; the shape of the second pressurizing functional member 22 and the second opening function portion 23 are symmetrical to the shape of the first pressurizing functional member 12 and the first opening function member 13, thereby facilitating control over pressurization and expansion of the rod. Certainly, the shape of the function portions on the first forceps body 1 and the second forceps body 2 can also be arranged to any other shape meeting the requirement of the using functions of the forceps. The U-shaped clamping slots which are perpendicular to the working faces of the first pressurizing functional member 12 and the first opening function member 13 are arranged in the first pressurizing functional member and the first opening function member, and the corresponding U-shaped clamping slots are also arranged in the second pressurizing functional member 22 and the second opening function portion 23. Certainly, the specific design form of the U-shaped clamping slots can also be determined according to the shape of the rod, and can be any other proper form. The opening size of the above U-shaped clamping slots can be determined according to the outer diameter of the specific rod; in order to prevent the U-shaped clamping slots from being worn by the rod, the wear resistant layers can be coated on the walls of the U-shaped clamping slots.

Figure 2:
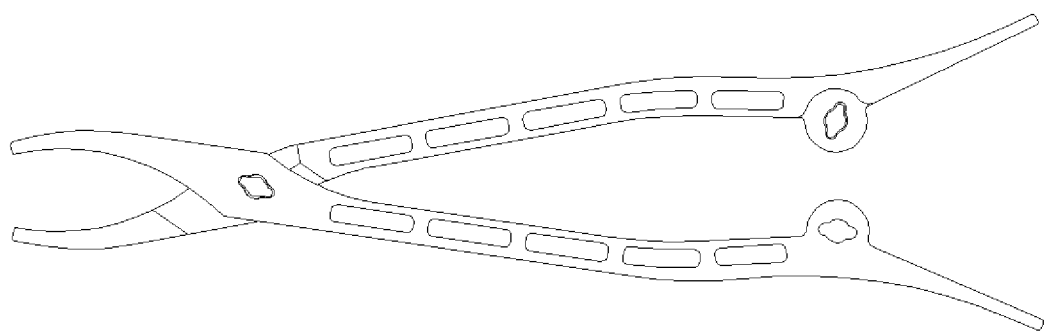
FIG. 2 is a structure diagram of the pressurized state of the dual-purpose forceps.

FIG. 2 is a structure diagram of the pressurized state of the dual-purpose forceps. When the first pressurizing connecting member 14 on the first forceps body 1 and the second pressurizing connecting member 24 on the second forceps body 2 can be rotated through the articulated shaft 3 freely and the first opening connecting member 15 on the first forceps body 1 is disengaged from the second opening connecting member 25 on the second forceps body 2, the first pressurizing connecting member 12 and the second pressurizing connecting member 22 can reduce the spacing between the screws through the U-shaped slots at the tail ends of the first pressurizing connecting member and the second pressurizing connecting member.

Figure 3:
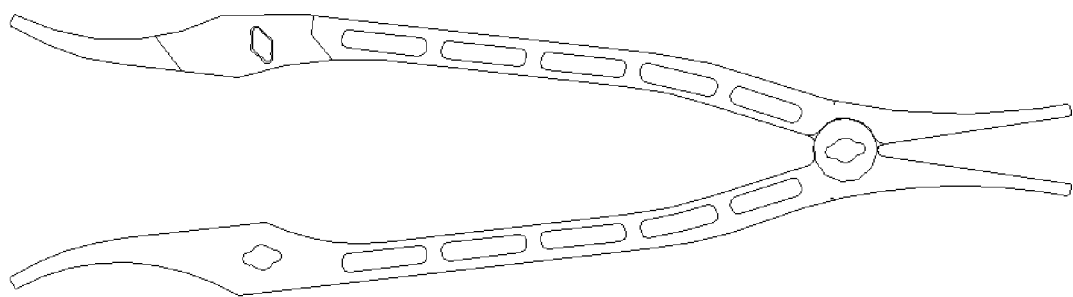
FIG. 3 is a structure diagram of the opening state of the dual-purpose forceps.
Figure 4:
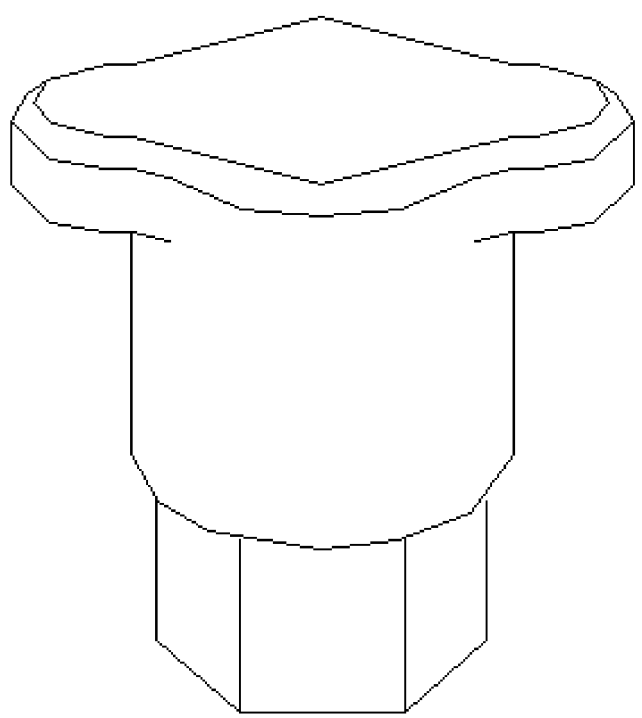
FIG. 4 is a structure diagram of the articulated shaft of the dual-purpose forceps. 1-first forceps body; 11-first handheld member; 12-first pressurizing functional member; 13-first opening function member; 14-first pressurizing connecting member; 15-first opening connecting member; 2-second forceps body; 21-second handheld member; 22-second pressurizing functional member; 23-second opening function portion; 24-second pressurizing connecting member; 25-second opening connecting member; 3-articulated shaft.

FIG. 3 is a structure diagram of the opening state of the dual-purpose forceps. When the first opening connecting member 15 on the first forceps body 1 and the second opening connecting member 25 on the second forceps body 2 can be rotated through the articulated shaft 3 freely and the first pressurizing connecting member 14 on the first forceps body 1 is disengaged from the second pressurizing connecting member 24 on the second forceps body 2, the spacing between the screws through the U-shaped slots at the tail ends of the first pressurizing connecting member and the second pressurizing connecting member.

The above description of the disclosed embodiments enables those skilled in the art to achieve or use the dual-purpose forceps. Different kinds of modifications for these embodiments are apparent to those skilled in the art, and general principles defined in this paper can be achieved in other embodiments without separating from the spirit or range of the invention. Thus, the invention is not limited to the embodiments shown in this paper, but needs to meet the widest range which is consistent with the principles and novel features disclosed in this paper.

The invention claimed is:

1. A pair of dual-purpose forceps comprising:
a first forceps body including a first handheld member, a first pressurizing functional member which is disposed at a first lengthwise end of the first forceps body, a first opening function member which is disposed at a second lengthwise end of the first forceps body, a first opening connecting member which is disposed at a transition area between the first handheld member and the first opening function member, and a first pressurizing connecting member which is disposed at a transition area between the first handheld member and the first pressurizing functional member; and
a second forceps body including a second handheld member, a second pressurizing functional member which is disposed at a first lengthwise end of the second forceps body and corresponds to the first pressurizing functional member, a second opening function portion which is disposed at a second lengthwise end of the second forceps body and corresponds to the first opening function member, a second opening connecting member which is disposed at a transition area between the second handheld member and the second opening function portion and corresponds to the first opening connecting member, and a second pressurizing connecting member which is disposed at a transition area between the second handheld member and the second pressurizing functional member and corresponds to the first pressurizing connecting member,
wherein the first forceps body is pivotably connected to the second forceps body by (a) the first opening connecting member being pivotably connected to the second opening connecting member while the first pressurizing connecting member and the second pressurizing connecting member are unconnected to each other or by (b) the first pressurizing connecting member being pivotably connected to the second pressurizing connecting member while the first opening connecting member and the second opening connecting member are unconnected to each other,
when the first forceps body is connected with the second forceps body through the first pressurizing connecting member and the second pressurizing connecting member and the first handheld member and the second handheld member move towards each other, the first pressurizing functional member and the second pressurizing functional member also move towards each other to perform pressurizing, and
when the first forceps body is connected with the second forceps body through the first opening connecting member and the second opening connecting member and the first handheld member and the second handheld member move towards each other, the first opening function member and the second opening function portion move away from each other to perform opening.

2. The dual-purpose forceps according to claim 1, further including a first articulated shaft for pivotably connecting the first pressurizing connecting member to the second pressurizing connecting member and a second articulated shaft for pivotably connecting the first opening connecting member to the second opening connecting member.

3. The dual-purpose forceps according to claim 2, wherein each articulated shaft has a head with an outer edge having a non-circular shape, one of the first pressurizing connecting member and the second pressurizing connecting member has a hinge hole with a non-circular shape formed therein for pivotably receiving the first articulated shaft, and one of the first opening connecting member and the second opening connecting member has a hinge hole with a non-circular shape formed therein for pivotably receiving the second articulated shaft.

4. The dual-purpose forceps according to claim 3, wherein each of the non-circular shapes is a rhombus.

5. The dual-purpose forceps according to claim 4, including relief slots or relief holes formed in the first handheld member and the second handheld member.

6. The dual-purpose forceps according to claim 5, wherein the first forceps body and the second forceps body are both made from ixef 1022 plastic.

7. The dual-purpose forceps according to claim 3, wherein a wear-resistant layer is formed on an inner wall of each hinge hole.

8. The dual-purpose forceps according to claim 7, including relief slots or relief holes formed in the first handheld member and the second handheld member.

9. The dual-purpose forceps according to claim 8, wherein the first forceps body and the second forceps body are both made from ixef 1022 plastic.

10. The dual-purpose forceps according to claim 3, including relief slots or relief holes formed in the first handheld member and the second handheld member.

11. The dual-purpose forceps according to claim 2, including relief slots or relief holes formed in the first handheld member and the second handheld member.

12. The dual-purpose forceps according to claim 1, including relief slots or relief holes formed in the first handheld member and the second handheld member.

13. A pair of dual-purpose forceps comprising:
a first forceps body including a first handheld member, a first pressurizing functional member which has an arcuate shape, a first opening function member which has an approximately linear shape, a first opening connecting member which is disposed at a transition area between the first handheld member and the first opening function member, and a first pressurizing connecting member which is disposed at a transition area between the first handheld member and the first pressurizing functional member; and
a second forceps body including a second handheld member, a second pressurizing functional member which has an arcuate shape and corresponds to the first pressurizing functional member, a second opening function portion which has an approximately linear shape and corresponds to the first opening function member, a second opening connecting member which is disposed at a transition area between the second handheld member and the second opening function portion and corresponds to the first opening connecting member, and a second pressurizing connecting member which is disposed at a transition area between the second handheld member and the second pressurizing functional member and corresponds to the first pressurizing connecting member,
wherein the shape of the second pressurizing functional member and the shape of the second opening function portion are symmetrical to the shape of the first pressurizing functional member and the shape of the first opening function member, respectively, when the first forceps body is connected with the second forceps body through the first pressurizing connecting member and the second pressurizing connecting member and the first handheld member and the second handheld member move towards each other, the first pressurizing functional member and the second pressurizing functional member also move towards each other to perform pressurizing, and when the first forceps body is connected with the second forceps body through the first opening connecting member and the second opening connecting member and the first handheld member and the second handheld member move towards each other, the first opening function member and the second opening function portion move away from each other to perform opening.

14. The dual-purpose forceps according to claim 13, including relief slots or relief holes formed in the first handheld member and the second handheld member.

15. A pair of dual-purpose forceps comprising:

a first forceps body including a first handheld member, a first pressurizing functional member, a first opening function member, a first opening connecting member which is disposed at a transition area between the first handheld member and the first opening function member, and a first pressurizing connecting member which is disposed at a transition area between the first handheld member and the first pressurizing functional member, wherein clamping slots which are perpendicular to working faces of the first pressurizing functional member and the first opening function member are formed in the first pressurizing functional member and the first opening function member; and a second forceps body including a second handheld member, a second pressurizing functional member which corresponds to the first pressurizing functional member, a second opening function portion which corresponds to the first opening function member, a second opening connecting member which is disposed at a transition area between the second handheld member and the second opening function portion and corresponds to the first opening connecting member, and a second pressurizing connecting member which is disposed at a transition area between the second handheld member and the second pressurizing functional member and corresponds to the first pressurizing connecting member, wherein clamping slots are also formed in working faces of the second pressurizing functional member and the second opening function portion, wherein when the first forceps body is connected with the second forceps body through the first pressurizing connecting member and the second pressurizing connecting member and the first handheld member and the second handheld member move towards each other, the first pressurizing functional member and the second pressurizing functional member also move towards each other to perform pressurizing, and when the first forceps body is connected with the second forceps body through the first opening connecting member and the second opening connecting member and the first handheld member and the second handheld member move towards each other, the first opening function member and the second opening function portion move away from each other to perform opening.

16. The dual-purpose forceps according to claim 15, wherein each of the clamping slots is U shaped.

17. The dual-purpose forceps according to claim 16, including relief slots or relief holes formed in the first handheld member and the second handheld member.

18. The dual-purpose forceps according to claim 17, wherein the first forceps body and the second forceps body are both made from ixef 1022 plastic.

19. The dual-purpose forceps according to claim 15, including relief slots or relief holes formed in the first handheld member and the second handheld member.

20. The dual-purpose forceps according to claim 19, wherein the first forceps body and the second forceps body are both made from ixef 1022 plastic.

* * * * *